United States Patent [19]

Davis

[11] 4,129,418

[45] Dec. 12, 1978

[54] DISCRIMINATING HALOGEN SENSOR

[75] Inventor: William D. Davis, Ballston Lake, N.Y.

[73] Assignee: General Electric Company, Schenectady, N.Y.

[21] Appl. No.: 879,157

[22] Filed: Feb. 21, 1978

[51] Int. Cl.² .......................................... G01N 27/62
[52] U.S. Cl. .................................................. 422/98
[58] Field of Search ............ 23/254 E, 255 E, 232 E, 23/254 EF, 254 R, 255 R, 232 R

[56] References Cited

U.S. PATENT DOCUMENTS 2,136,741  11/1938  Henne ........................... 23/254 R X
3,535,088  10/1970  Zimmermann ................... 23/254 E
3,607,096  9/1971   Hartmann ....................... 23/254 EF Primary Examiner—Robert M. Reese
Attorney, Agent, or Firm—Lawrence D. Cutter; Joseph T. Cohen; Marvin Snyder

[57] ABSTRACT

A halogen detector is disclosed herein in which the active alkali metal compound is independently heated thereby permitting the sensor to discriminate between halogen compounds of different thermal stabilities. Certain lesser stable halogen compounds such as Freon 22 and chloroform can be distinguished from more stable halogen compounds such as Freon 12 when such halogen compounds are present in air.

9 Claims, 2 Drawing Figures

DISCRIMINATING HALOGEN SENSOR

BACKGROUND OF THE INVENTION

This invention relates to detectors for sensing the presence of halogen compounds in air, such as those present in air because of refrigerant leaks for example. More particularly, this invention relates to those sensors in which a heated alkaline metal compound is employed as a source of ionizable vapors.

There is a large class of chemical compounds containing halogens which are useful and used in a variety of refrigeration equipment including air conditioners and refrigerators found both in industrial and home settings. These compounds may be either aromatic or aliphatic carbon-halogen liquids or gases typically having low boiling points. To guarantee and test for the mechanical integrity of systems containing such compounds, halogen leak detectors have been developed.

In a typical halogen leak detector, a cylinder of a powdered alkaline metal compound is contained within a thin wrapping of platinum foil which serves as a cathode in the detector. This cylindrical cathode is surrounded by a coil of heated platinum wire which serves as an anode in the detector. Also typically present in this structure is a slotted ceramic cylindrical spacer serving both to hold the cathode and to support the platinum anode windings. This structure which is typically approximately 1 inch long is disposed inside a glass, ceramic, or other heat-proof envelope through which the air to be sampled is passed. The anode of the detector is heated to a temperature of approximately 1,000° C. When air containing a halogen compound such as a leaking refrigerant passes through the detector an alkali metal halide in the vapor is thought to be formed which upon drifting to the heated anode, is ionized thereby generating positive ions which migrate back to the cathode which is held at a negative potential. This ion migration results in a small, but detectable, current produced in an external circuit. The increase in current that results in the external circuit depends upon the concentration of the halogen present in the air as measured in parts per million (ppm).

While the exact mechanism under which this current increase occurs is not fully understood, the detector described above functions well and reliably in detecting halogens. However, there are several limitations. In particular, the detector, as described, is not capable of discriminating between different halogens that may be present. This lack of discriminatory ability is due in large part to the fact that there is only a single heating source maintained at a relatively high temperature of 1,000° C. at which almost all halogens react to activate the detector. Thus, halogen compounds present in the air which are relatively stable compounds as well as those compounds which are relatively unstable will activate the detector. In the prior art detector described above, the source, that is the alkali metal compound, is heated by the anode winding which must be kept at a high temperature in order to produce the necessary amount of reaction and ionization. However, while some degree of thermal activation must be provided to the source, it is not necessary that it be heated to the same temperature as the anode.

SUMMARY OF THE INVENTION

It has been found that certain halogen compounds present in gaseous form in the atmosphere react directly with the alkaline metal compound at temperatures below 1,000° C., namely, at temperatures of from approximately 500° C. to approximately 600° C. These other, less thermally stable halogens include Freon 22 ($CHClF_2$) and chloroform ($CHCl_3$) among others. Other halogen compounds such as Freon 12 possess a higher degree of thermal stability and therefore require higher detector operating temperatures to effect a change in the current flowing in a circuit which includes the anode and cathode of the detector.

In accordance with one embodiment of the invention herein, means are provided for keeping the alkali metal compound source at a lower temperature, such as 500° C., which is sufficient to produce a detectable change in the current when less stable halogen compounds are found in the air flowing through the detector envelope. This temperature range, however, is not sufficient to cause a change in current when the more stable halogen compounds are present in the air flow.

Accordingly, it is an object of this invention to provide a halogen sensor capable of discriminating between relatively unstable halogen compounds such as Freon 22 and chloroform and other more relatively stable halogen compounds such as Freon 12.

DETAILED DESCRIPTION OF THE INVENTION

Figure 1:
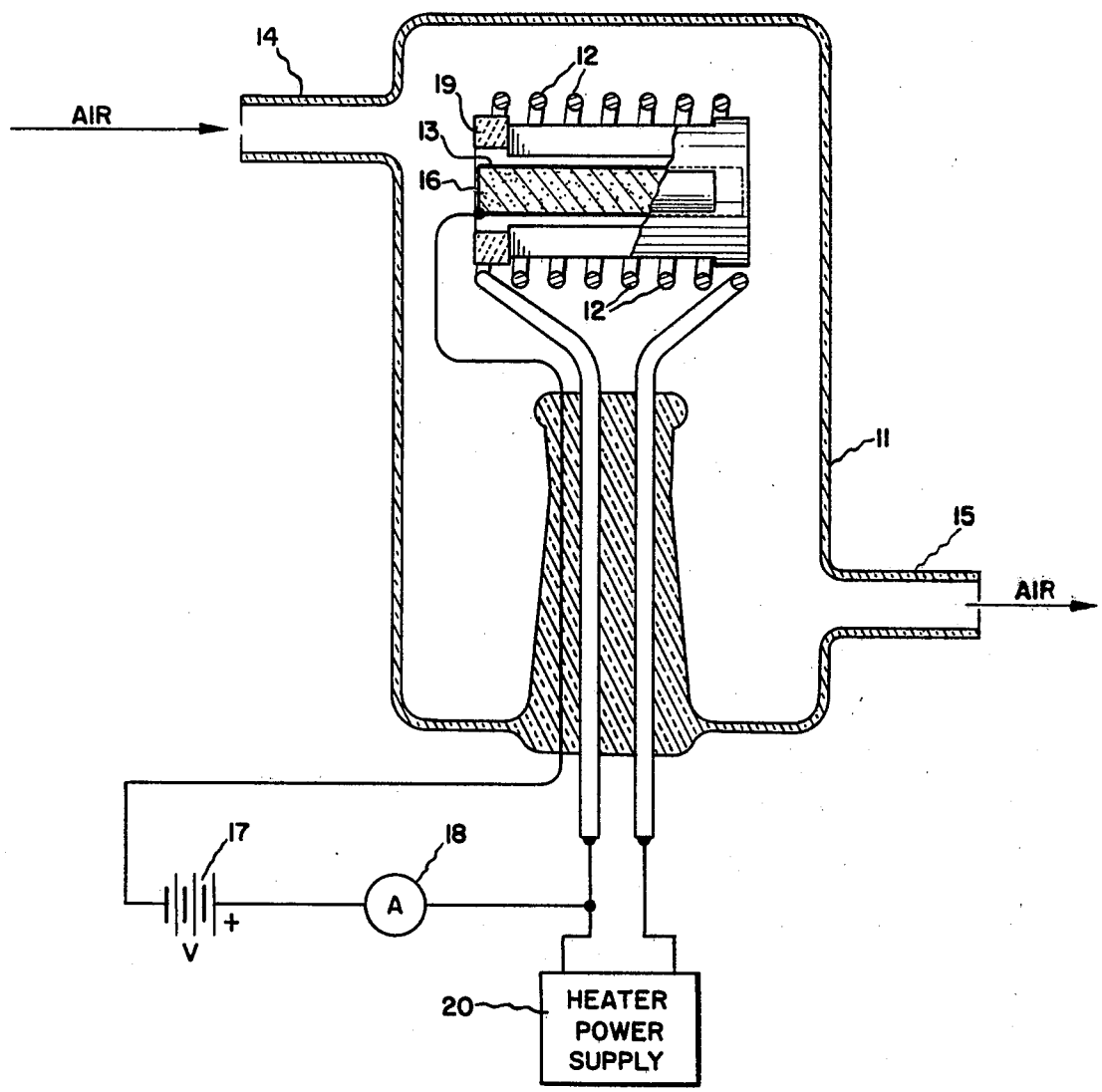
FIG. 1 is a partial sectional elevation view of a prior art halogen sensor.

In a typical halogen sensor of prior art configurations, such as that shown in FIG. 1, an alkali metal compound 16 is contained within a cylindrical platinum foil wrapper 13 together forming a cathode element which is maintained at a negative potential by dc voltage source 17 which maintains said cathode at a typical potential of approximately 180 volts below the potential of the heated filament anode 12, typically composed of platinum windings. These windings 12 are maintained at a temperature of approximately 1,000° C. by d.c. heater power supply 20. Also typically contained in prior art halogen detectors is a slotted ceramic cylinder 19 used to both contain the cathode and to support the anode windings. This anode-cathode support structure is typically mounted on a glass support stem disposed within a heat resistant envelope 11 which typically possesses an air inlet 14 and air outlet 15. If the air passing through the detector contains a halogen compound, then as described above, the ionization level increases and a greater amount of current flows through a circuit comprising the cathode, a dc voltage source 17, an ammeter 18, and the anode 12.

Figure 2:
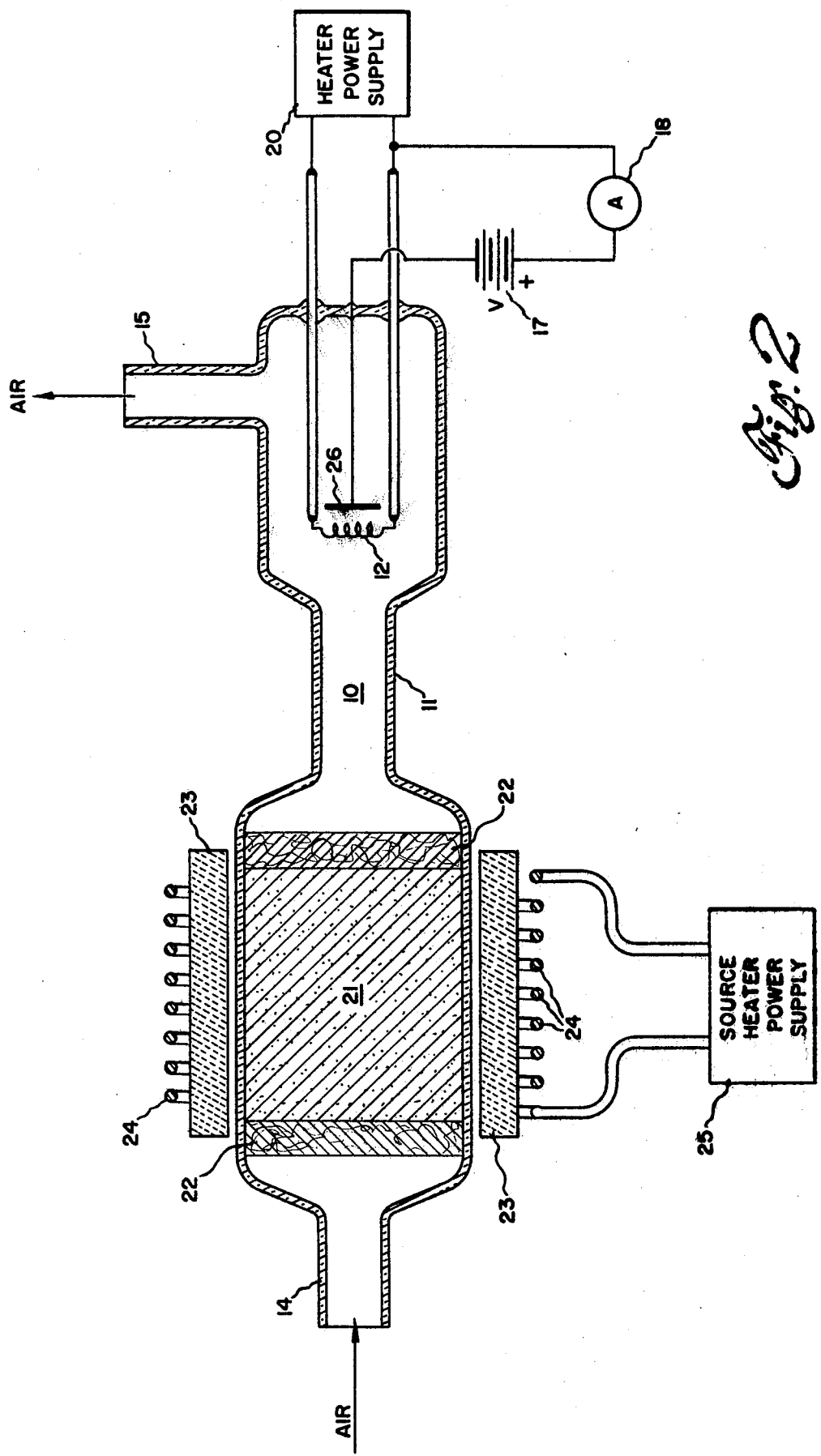
FIG. 2 is a partial sectional elevational view of a halogen sensor in accordance with one embodiment of the present invention.

FIG. 2 illustrates one embodiment of the present invention in which certain limitations in the prior art halogen detectors are overcome. In particular, in FIG. 2, it is to be noted the alkali metal compound source 21 is no longer disposed in an immediately proximate relationship to the heated anode filament 12 which is still maintained at a temperature of approximately 1,000° C. by heater supply 20. Instead of FIG. 2, the alkali metal compound is disposed in a relatively distinct region of the detector envelope 11 and maintained at a temperature of from approximately 500° C. to approximately 600° C. by a separate source heater power supply 25.

The alkali metal compound 21, typically in powdered form, together with porous retaining plugs 22 typically composed of a material such as quartz wool serve to approximately define a source region of the detector envelope. The heated filament 12 together with cathode 26 and their corresponding support structures serve to define another area within the envelope 11 referred to as the electrode region. These two regions are in relative thermal isolation so that the filament 12 and the alkali metal compound source 21 may be maintained at different temperatures.

The envelope of the detector is typically composed of a glass or ceramic material and primarily serves as a heat resistive containment means for the source and electrode and further serves as the channel for the passage of air. The envelope is provided with an air inlet 14 and an air outlet 15 for the passage of air potentially containing a halogen compound through the source region to the electrode region and back out again to the atmosphere. Also provided in the quartz or ceramic envelope 11 is a reduced neck 10 which serves the dual function of facilitating the unidirectional passage of air and other vapor molecules through the envelope and also serves to provide a certain degree of thermal isolation between the two regions of the detector.

The source region of the detector envelope is surrounded by a ceramic material 23 which in turn is surrounded or contains heater windings 24 composed of any standard resistive heating wire. These heater windings 24 are heated by a current provided by a separate source heater power supply 25 so as to maintain the source 21 within the envelope at a temperature of from approximately 500° C. to approximately 600° C. The quartz or ceramic support 23 serves not only to support the windings but serves to more evenly distribute the heat across the source region of the detector. The resistive heater windings even may be surrounded by the ceramic support 23 or perhaps the support may contain slots or channels therein. The details of the heater construction for the alkali metal compound source are not critical. Any means capable of maintaining the source 21 at a uniform temperature in the range desired is sufficient.

A number of different compounds may be used as the alkali metal compound source. Typical of these are the alkali metal aluminates, carbonates and silicates. In particular, sodium carbonate and rubidium carbonate are employed. In addition, alumina impregnated with sodium carbonate is also used as a source material.

The electrode structure is disposed in an end of the enclosing envelope 11 are proximal to the air outlet 15. The source region is similar to the electrode structure in FIG. 1 with several important exceptions to be discussed below. In the electrode structure of FIG. 2 the cathode need not be composed of platinum as is the cathode 16 of FIG. 1. However, the same heater power supply 20 as used in FIG. 1 is used in the configuration in FIG. 2 to maintain the anode at a temperature of approximately 1,000° C. The heated anode is typically composed of platinum wire but other material compositions such as palladium and iridium are possible. In the novel embodiment shown in FIG. 2, it is not necessary for the cathode to be composed of any particular metal such as platinum. It is sufficient that the cathode merely be composed of a metal which is a good electrical conductor.

A dc voltage source 17 operating at voltage V which is typically approximately 180 volts is connected to the cathode of the detector and said dc supply voltage is also in series with an ammeter 18 through which it is connected to one side of the anode filament, preferably the ungrounded side. Thus, a current loop is formed including the cathode 26, the dc voltage source 17, the ammeter 18, and the anode 12. An increase in the concentration of halogen compound in the air entering the envelope 11 causes the increase in the alkali halides reaching the heated anode filament 12 and thereby produces an increase in current in this external circuit.

By independently heating the source region of the halogen detector to temperatures of only between approximately 500° C. and 600° C., it is possible to detect the presence of halogen compounds in the air which are relatively thermally unstable, such as the Freon 22 and chloroform, amongst others. These less stable halogens are more capable of interacting with the alkali metal compound source at lower temperatures than are the more stable halogen compounds, such as Freon 12. In this mode of operation, the detector is thereby able to discriminate among possible halogen compounds contained in the ambient air which is fed through the detector envelope.

In addition to the above-mentioned ability to discriminate among certain halogen compounds, the structure disclosed herein also possesses certain other advantages. In particular, the structure shown in FIG. 2 requires less platinum than the prior art structure shown in FIG. 1 which requires not only a platinum anode filament but a platinum foil wrapping around the alkali metal compound source. The structure herein only requires expensive platinum in the anode filament. In addition, the structure as shown in FIG. 1 continually heats the alkali metal compound source contained within the platinum foil to a high temperature at or near the 1,000° C. temperature of the anode filament 12. At these temperatures, the life of the source is greatly reduced. However, in the configuration shown in FIG. 2, the alkali metal source can be provided in much greater quantities and need not be exposed to the extremely high temperatures of the anode filament. Thus, the expected life of the detector shown in FIG. 2 is greatly increased. Furthermore, the detector is shown in FIG. 2, partly due to the greater amounts of alkali metal source provided, exhibits a greater sensitivity to halogen compounds in the air. This sensitivity is measured in microampere increases in current per ppm of halogen compound. It should be noted that it is the increase in current which is used to indicate the presence of a halogen, partly since standard atmospheric air without any halogens present produces a background current reading of between approximately 1 and 2 microamperes. In addition, if desired, the source heater power supply 25 may be made to be variable so as to produce a higher temperature than suggested above so that the relatively more stable halogen compounds may then be detected. Even if the source region is maintained at a temperature of 1,000° C., by an adjustable source heater power supply, the independent nature of this power supply permits operation at this higher temperature of less extended periods of time and thereby serves to prolong the life of the alkali metal compound source.

While this invention has been described with reference to particular embodiments and examples, other modifications and variations will occur to those skilled in the art in view of the above teachings. Accordingly, it should be understood that within the scope of the appended claims, the invention may be practiced otherwise than is specifically described.

The invention claimed is:

1. A discriminating halogen detector comprising:
    an envelope with an air inlet and an air outlet at substantially opposite ends thereof, said envelope enclosing a source region and an electrode region, said source region being proximal to the air inlet and said electrode region being proximal to the air outlet, said source region internally communicating with said electrode region;
    an alkali metal compound source contained in said source region;
    means to independently heat said source region;
    a heated anode disposed in said electrode region capable of ionizing alkali vapors generated by said alkali metal compound source; and
    a cathode disposed in said electrode region adjacent to but not contacting said anode, whereby ions generated at the heated anode migrate to said cathode thereby forming a detectable current in an external circuit in response to halogens contained in air passing through the source region of the detector.

2. The detector of claim 1 in which the alkali metal compound source is selected from the group consisting of the alkali metal carbonates, the alkali metal silicates and the alkali metal aluminates.

3. The detector of claim 1 in which the alkali metal compound is selected from the group consisting of sodium carbonate and rubidium carbonate.

4. The detector of claim 1 in which the independent means to heat said source region operates at a temperature between approximately 500° C. and approximately 600° C.

5. The detector of claim 1 in which the means to independently heat said source region is adjustable.

6. The detector of claim 1 in which the anode is heated to a temperature of approximately 1,000° C.

7. A discriminating halogen detector system comprising:
    the halogen detector of claim 1;
    external circuit means to bias said cathode at a negative potential with respect to said anode; and
    means to detect increases in current in said external circuit.

8. The detector of claim 1 in which the anode is a filament composed of a material selected from the group consisting of platinum, iridium, and palladium.

9. The halogen detector system of claim 8 in which the biasing means operates to maintain the said anode and cathode at a potential difference of approximately 180 dc volts.

* * * * *